US010853518B2

(12) United States Patent
Rosenberg et al.

(10) Patent No.: US 10,853,518 B2
(45) Date of Patent: Dec. 1, 2020

(54) SYSTEMS AND METHODS FOR PROVIDING SECURE ACCESS TO DATA USING ENCRYPTED CODES

(71) Applicant: MEDICOM TECHNOLOGIES INC., Raleigh, NC (US)

(72) Inventors: Michael David Rosenberg, Raleigh, NC (US); Brandon Joseph Gottfried, Raleigh, NC (US); Chase Spencer Ballard, Raleigh, NC (US)

(*) Notice: Subject to any disclaimer, the term of this patent is extended or adjusted under 35 U.S.C. 154(b) by 198 days.

(21) Appl. No.: 16/195,918

(22) Filed: Nov. 20, 2018

(65) Prior Publication Data

US 2019/0156055 A1 May 23, 2019

Related U.S. Application Data

(60) Provisional application No. 62/589,271, filed on Nov. 21, 2017.

(51) Int. Cl.
| | | |
|---|---|---|
| G06F 21/62 | (2013.01) | |
| G06F 21/60 | (2013.01) | |
| G16H 10/60 | (2018.01) | |
| H04L 29/06 | (2006.01) | |
| G16H 30/20 | (2018.01) | |
| H04L 9/32 | (2006.01) | |
| G06F 16/9535 | (2019.01) | |
| H04L 9/08 | (2006.01) | |

(52) U.S. Cl.
CPC ...... *G06F 21/6245* (2013.01); *G06F 16/9535* (2019.01); *G06F 21/602* (2013.01); *G16H 10/60* (2018.01); *G16H 30/20* (2018.01); *H04L 9/0894* (2013.01); *H04L 9/3213* (2013.01); *H04L 9/3215* (2013.01); *H04L 9/3228* (2013.01); *H04L 9/3271* (2013.01); *H04L 63/0428* (2013.01); *H04L 2209/88* (2013.01)

(58) Field of Classification Search
CPC .................................................. G06F 21/6245
USPC ............................................................ 713/155
See application file for complete search history.

(56) References Cited

U.S. PATENT DOCUMENTS

| | | | | |
|---|---|---|---|---|
| 8,960,555 B1* | 2/2015 | Walton, III | ...... | G06K 19/06037 235/487 |
| 2004/0204965 A1* | 10/2004 | Gueck | .................... | G16H 30/20 705/3 |

(Continued)

OTHER PUBLICATIONS

Sharghi et al., Federated Service-based Authentication Provisioning for Distributed Diagnostic Imaging Systems, IEEE, 2015, 28th International Symposium on Computer-Based Medical Systems, pp. 345-347. (Year: 2015).*

(Continued)

*Primary Examiner* — Peter C Shaw

(57) ABSTRACT

The present invention relates to directly and securely transferring encrypted medical data between parties, wherein a sender generates an encrypted access code. The access code is provided to a recipient who can then view the medical data without requiring cloud and virtual private network infrastructures, and which eliminate the need for medical data to be stored on physical media and physically carried to a recipient's location. The invention empowers patients to view, share, and manage their medical data, and facilitates the preservation of the continuum of care.

7 Claims, 12 Drawing Sheets

(56) References Cited

U.S. PATENT DOCUMENTS

| | | | | |
|---|---|---|---|---|
| 2007/0055538 A1* | 3/2007 | Burton | .................. | G06Q 50/22 |
| | | | | 705/2 |
| 2012/0203104 A1* | 8/2012 | Urness | .................. | A61B 8/461 |
| | | | | 600/443 |
| 2013/0006867 A1* | 1/2013 | Dove | ..................... | H04L 9/083 |
| | | | | 705/51 |

OTHER PUBLICATIONS

Striletchi et al., A Secured Distributed Medical Application Endowed with Image Processing Facilities, IEEE, 2010, 978-1-4244-8460-7/10, pp. 345-348. (Year: 2010).*

* cited by examiner

MEDICOM Patient Link

View exams

You have been logged out due to inactivity

Enter access code

☐ - ☐ - ☐

Date of birth

| Month ▽ | Day | Year (e.g. 1996) |

Next

FIG. 5

Share Your Exams

Click the checkbox beside the exams you wish to share.

← Back to My Exams

| | Exam date ▾ | Exam | Patient |
|---|---|---|---|
| ☐ | 02/12/1953<br>3:44 PM | TOMO SCR<br>Acc: 149742856<br>Ref Phys: Mary Johns   Institution: Portland East | Joann Rivera<br>DOB: 02/12/1952<br>MRN: 2636782 |
| ☐ | 05/21/2016<br>3:44 PM | CT HEAD<br>Acc: 163845285<br>Ref Phys: Mary Johns   Institution: Portland East | Joann Rivera<br>DOB: 02/12/1952<br>MRN: 2636782 |

FIG. 7

Share Your Exams

Enter the email address of your friend or family member below and Medicom will send an email with electronic access to your exams.

Recipient's Email

Confirm Recipient's Email

Subject Line

Notes

Send

← Back to My Exams

FIG. 8

Share Your Exams

Enter the fax number of your doctor or healthcare provider below and Medicom will send a fax with electronic access to your exams.

Recipient's Fax Number

Confirm Recipient's Fax Number

Attention

Notes *(Optional)*

Send

← Back to My Exams

SYSTEMS AND METHODS FOR PROVIDING SECURE ACCESS TO DATA USING ENCRYPTED CODES

RELATED APPLICATIONS

This application claims the benefit of U.S. Provisional Patent Application No. 62/589,271 entitled "SYSTEM AND METHOD FOR PROVIDING SECURE ACCESS TO DATA USING ENCRYPTED CODES" filed on Nov. 21, 2017 and which is commonly owned, the disclosure of which is incorporated herein by reference in its entirety.

BACKGROUND OF THE INVENTION

It is common place in today's environment to find medical care providers with an assortment of medical devices that produce digital images that need to be subsequently analyzed by a specialist to identify potential health issues with the highest confidence. Such fields making use of medical imaging include, for example, radiology, cardiology imaging, and radiotherapy, as well as ophthalmology and dentistry. Transmission of scanned and captured medical images, or studies, are complicated by the fact that they are subject to Health Insurance Portability and Accountability Act of 1996 ("HIPAA") requirements, whereby all entities that take possession of such studies, even when ephemeral, must be pre-qualified as HIPAA compliant. One solution to this problem is to establish a virtual private network ("VPN") between the medical provider and the diagnostic facility or lab. However, this solution suffers from complexity and cost. Installing a VPN between two locations commonly means segregating the network at both ends to limit what information or data each part has access to. While implementing a VPN between a single set of locations may seem straightforward, it quickly become less tractable when a single provider needs to communicate over VPN with a plurality of other providers at various locations. Such a scenario requires creating a separate VPN zone for each of the provider, and requires installing, configuring, and managing a separate VPN for each provider. As a result, scalability problems quickly arise as medical practices, patient volumes, and imaging throughput grows.

Another popular method of transmitting medical data is to store it on a CD, DVD, or other media and physically shipping the media via postal mail, couriers, and/or messenger services. In some extreme cases, CDs are taped to patients as they are leaving one facility and in-route to another, or the CD is simply dropped into a patient stretcher, unsecured and prone to loss and damage.

In previous years, when communication and data networks were generally much slower, and bandwidth was limited and costly, such antiquated methods held appeal. However, physical media suffers from lack of immediacy given that it is generally quicker to send data over today's networks than to suffer the delays and risks involved in physical transit. Physical media is also prone to being damaged, stolen, or lost in transit, and inherently carries the risk of accidental or unwanted exposure of patient information and records, thereby compromising HIPAA compliance and patient confidentiality.

What is needed is a system that is efficiently installed and configured, and which complies with all regulations regarding privacy and security, and which provides for immediate delivery of medical data with confirmation and traceability. As such, the present invention empowers patients to view, share, and manage their medical data by distributing an access code to third-parties whom they wish to provide access. In one aspect, patients can securely share access with physicians, caretakers, and clinicians which ultimately facilitates the preservation of the continuum of care.

SUMMARY OF THE INVENTION

In an embodiment, the present invention relates to a system for providing secure access to medical data, comprising: a database coupled to a network, wherein the database is configured to store medical data, wherein the medical data consists of a plurality of medical studies; a user interface coupled to the database via the network, wherein the user interface is configured to receive a query related to at least one property of the medical data; and a server coupled to the user interface via the network, wherein the server is configured to receive the query from the user interface, and further configured to identify a matching medical study that matches the at least one property, the server further configured to generate an access code that allows secure access to the matching medical study by a remote computing device via a communication channel.

In yet another embodiment, the present invention relates to a method of providing secure access to a medical image study, comprising: generating, by a server, an encrypted access code containing a study identifier and at least one network location; receiving, from a user device, an instruction to transmit the access code to at least one recipient device, wherein the transmission medium is selected from a group consisting of electronic mail, facsimile, SMS messaging, direct messaging, and secure messaging, the instruction further including a recipient address; and transmitting, by the server, the access code to the recipient device based on the transmission medium specified in the instruction, wherein the study identifier is associated with a plurality of diagnostic images stored on a plurality of databases coupled to the server, and wherein the network location corresponds to network addresses of databases with diagnostic images containing the study identifier, and wherein the recipient device is allowed access to the diagnostic images via an encapsulated viewer upon the recipient device transmitting the access code to the server.

In yet another embodiment, the present invention relates to a system for providing secure access to medical data, comprising: a server comprising a communication transceiver configured to send and receive the medical data over a peer-to-peer communication channel, the server having a central processing unit (CPU) configured to: execute a first data transmission protocol that includes the steps of generating an access code and transmitting the access code to a recipient device, and a second data transmission protocol that includes the steps of encapsulating the medical data and transmitting the encapsulated medical data to the recipient device via direct messaging, wherein the CPU is configured to execute the first data transmission protocol if the recipient device is a not healthcare entity, and wherein the CPU is configured to execute the second data transmission protocol if the recipient device is a healthcare entity.

BRIEF DESCRIPTION OF THE DRAWING FIGURES

The accompanying drawing figures incorporated in and forming a part of this specification illustrate several aspects of the disclosure, and together with the description serve to explain the principles of the present invention.

FIG. 5 is an exemplary user interface for accessing a medical image study using an access code, according to an embodiment of the present invention;

FIG. 7 is an exemplary patient study image selection interface, according to an embodiment of the present invention;

FIG. 8 is an exemplary electronic mail sharing interface, according to an embodiment of the present invention;

FIG. 9 is an exemplary facsimile sharing interface, according to an embodiment of the present invention;

DETAILED DESCRIPTION

The description set forth below in connection with the appended drawings is intended as a description of presently preferred embodiments of the application and is not intended to represent the only forms in which the present application may be constructed and/or utilized. The description sets forth the functions and the sequence of steps for constructing and operating the application in connection with the illustrated embodiments. It is to be understood, however, that the same or equivalent functions and sequences may be accomplished by different embodiments that are also intended to be encompassed within the spirit and scope of this application.

The present invention is directed to a system and method for the storage and distribution of medical data, including, but limited to, medical records, images and other personal information such as a patient information record, including DICOM (Digital Imaging and Communications in Medicine) format medical images. While it is envisioned that the present invention is applicable to the electronic transmission and sharing of any records comprising both personal information and other information which is not personally identifiable (i.e., non-personal information), the present invention describes the system and method, by way of non-limiting example only, with particular applicability to medical data, and more specifically to medical image studies which are comprised of DICOM images.

The present invention is a network that makes it possible for medical data comprising personal information and other non-personal information to be delivered in mere seconds via a secure peer-to-peer communication network, instead of days or weeks through the use of manually burned CDs and DVDs, which are mailed using postal mail, couriers, and messenger services. Using the present invention, patient images, records, and documents not only reach their destination immediately upon a request by a recipient, but also in a more secure, efficient, and cost-effective manner.

Figure 1:
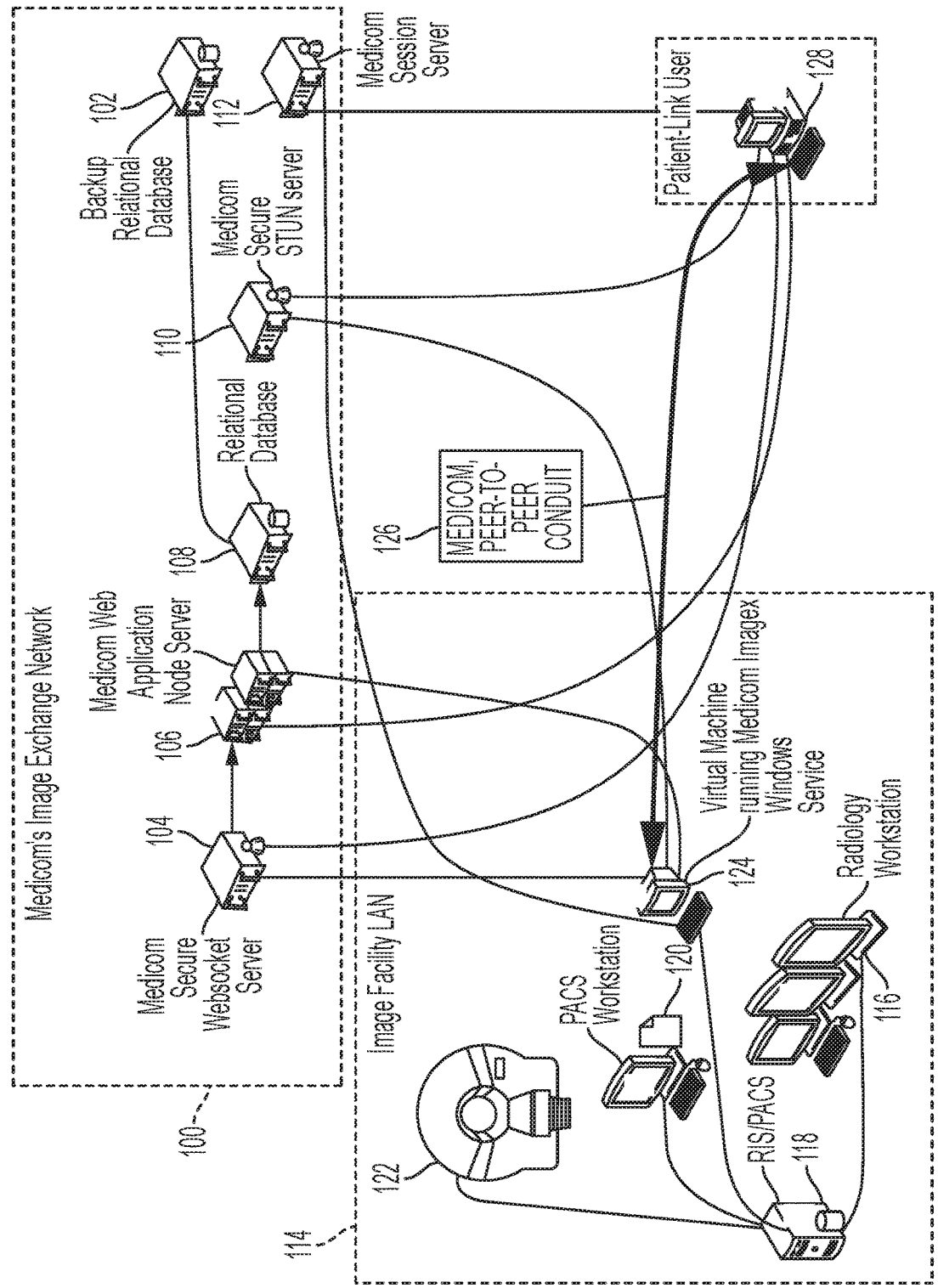
FIG. 1 is an exemplary network architecture diagram, according to an embodiment of the present invention.

FIG. 1 is an exemplary network architecture diagram, according to an embodiment of the present invention. The data exchange network 100 include various components, such as a backup relational database 102, a web socket server 104, a web application node server 106, a relational database 108, a secure STUN (Session Traversal of User Datagram Protocol [UPD] Through Network Address Translators [NATs]) server 110, and a session server 112.

The data exchange network 100 is preferably a distributed, public access network, such as the Internet, wherein a user device 128 and the web socket server 104 are capable of interacting with and through the data exchange network 100 using various protocols such as Transmission Control Protocol/Internet Protocol (TCP/IP), Hypertext Transport Protocol (HTTP), and File Transfer Protocol (FTP). However, those of ordinary skill in the art will appreciate that the data exchange network 100 is not limited thereto. The servers described herein can include a transmitter, receiver, transceiver, and/or any other communication interface that allows the servers to bi-directionally communication with other devices, components, and servers on the data exchange network 100 as well as located outside of the data exchange network 100. The servers can also include a local storage, central processing unit (CPU), and a file system. In yet another embodiment, the servers can be a cloud-based computing and storage network, such as that provided by the Amazon Web Services group at Amazon.com, Inc.

More specifically, the data exchange network 100 may be any type of network suitable to allow interaction between the user device 128 and the web socket server 104. For example, the data exchange network 100 may be a wired network, a wireless network, or any combination thereof. Further, the data exchange network 100 may include a distributed computing network, an intranet, a short-range mesh network, a local-area network (LAN) and/or a wide-area network (WAN), or any combination thereof. The data exchange network 100 may be comprised of wired and wireless elements. For example, the LAN may make use of WIFI in its many variations and the WAN may make use of cellular networks using technologies including, but not limited to, CDPD, CDMA, GSM, PDC, PHS, TDMA, FLEX, ReFLEX, iDEN, TETRA DECT, DataTAC, Mobitex, EDGE and other 2G, 3G, 4G and LTE technologies.

The web application node server 106 is configured to serve a web-based interface to a display on the user device 128. The node server 106 can include a combination of integrated software components and an allocation of computational resources, such as memory, multiple nodes, and processes on these nodes for executing the integrated software components on at least one processor, the combination of the software and computational resources being dedicated to performing a particular function on behalf of the user device 128. Resources from multiple nodes in the multi-node environment within the data exchange network 100 can be allocated to run the node server 106 software. A particular combination of the software on a node and the allocation of the resources from the node server 106 is referred to herein as a server instance or instance. Thus, the node server 106 can comprise multiple server instances that can run on multiple nodes. Several instances of the node server 106 can even run on the same node.

The web socket server 104 can verify connections on the data exchange network 100 using the relational database 108. The relational database 108 can be, for example, a MySQL relational database. The web socket server 104 can verify connections by referencing the relational database 108 comprising of entities (such as, for example, individuals, groups, medical providers, diagnostic providers, etc.) authorized in, for example, a patient's continuum of care.

The web socket server 104 is communicatively coupled to a STUN server 110. The STUN server 110 allows the user device 128 to determine its public address, the type of NAT the user device 128 is located behind, and the internet-side port associated by the NAT with a particular local port. This information is used to set up UDP communication between the user device 128 and a VoIP provider to establish a call between the two locations. The STUN protocol is defined in RFC 3489. In response to receiving the request for networking address of the user device 128, the STUN server 110 operates to determine the public networking address of the user device 128.

The web socket server 104 does not inherently retain the state of past requests from the user device 128. To solve this problem, application work flow is maintained by the session server 112, which bundles and stores session data related to accesses from any system node or device. Each time a user device 128 enters the data exchange network 100, the user device 128 can be given a new unique session ID. Session data representing a state of the user device 128 is stored in a memory in the session server 112. As each subsequent request associated with the user device 128 is received, the session data is retrieved from the session server 112 using the session ID. The subsequent request is then processed using the session data to provide a web-based interface to the user device 128. The session server 112 stores session data unique to each user device session accumulated over time, and over multiple web connections and instances.

The data exchange network 100 is communicatively coupled to an imaging facility 114 network, such as a LAN. The imaging facility 114 can include multiple devices, such as provider workstations 116, a picture archiving and communication systems (PACS) 118, a PACS workstation 120, and imaging equipment 122.

The imaging equipment 122 may include, but is not limited to, diagnostic and imaging equipment used for computed tomography (CT), fluoroscopy, magnetic resonance imaging (MM), magnetic resonance angiography (MRA), mammography, nuclear medicine, x-ray, positron emission tomography (PET), elastography, photo-acoustic imaging, echocardiograph and ultrasound studies.

At the imaging facility 114, the imaging equipment 122, PACS workstation 120, and provider workstations 116 are all communicatively coupled to the PACS 118 via the LAN. In addition, a virtual machine 124 running the data exchange network service is coupled to the PACS 114. The virtual machine 124 is further coupled to the data exchange network 100 and the user device 128 via a secure peer-to-peer communication channel 126.

The PACS 118 is a medical imaging technology that provides economical storage and convenient access to images from multiple modalities (i.e., imaging source machine types). Electronic images and reports are transmitted digitally via PACS 118; this eliminates the need to manually file, retrieve, or transport film jackets. The universal format for PACS image storage and transfer is DICOM. Non-image data, such as scanned documents, may be incorporated using consumer industry standard formats like Portable Document Format ("PDF") and Clinical Document Architecture ("CDA" or "C-CDA"), once encapsulated in DICOM.

The peer-to-peer communication channel 126 has been fully described in commonly owed U.S. patent application Ser. No. 15/361,319, filed on Nov. 25, 2016, and entitled, "METHODS AND SYSTEMS FOR PROVIDING SECURE AND AUDITABLE TRANSFER OF ENCRYPTED DATA BETWEEN REMOTE LOCATIONS", which is hereby incorporated by reference in its entirety.

Figure 2:
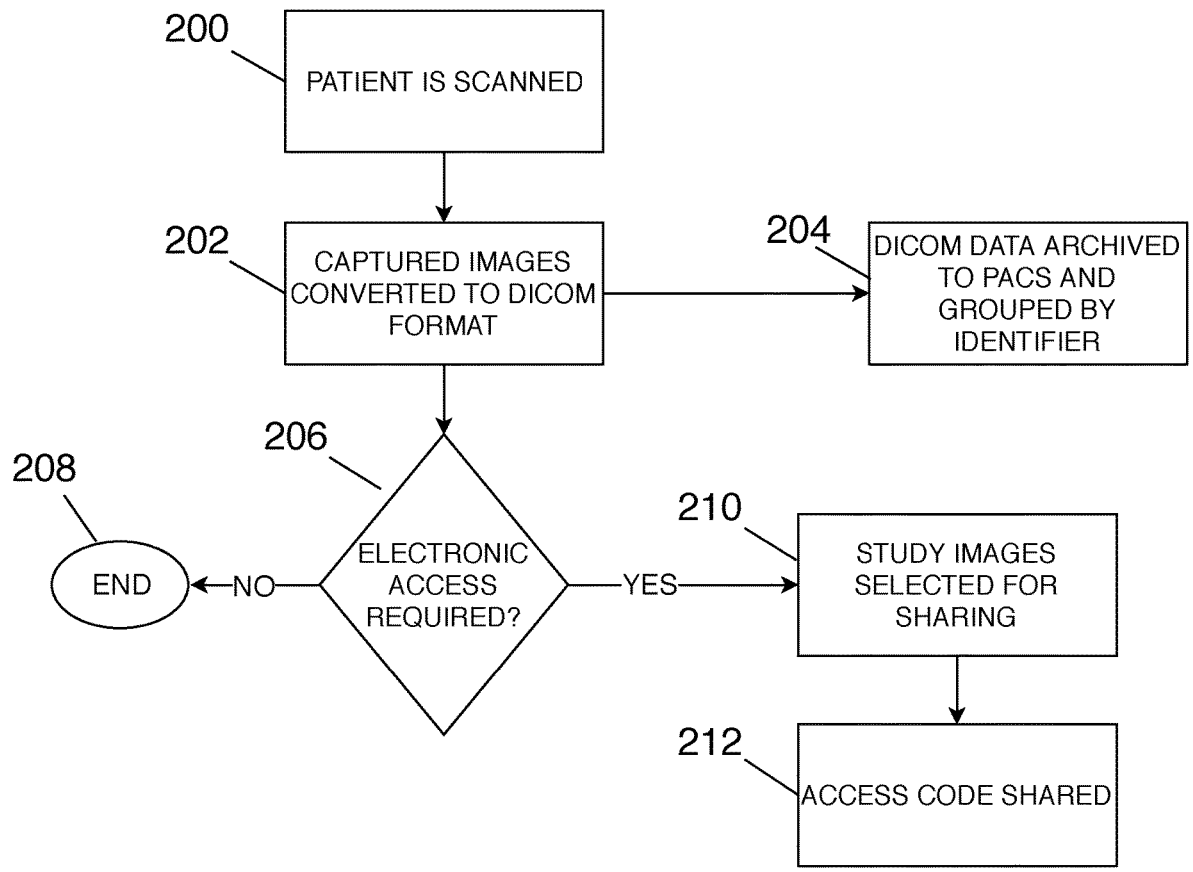
FIG. 2 is a flowchart illustrating an image capture and storage workflow for a medical image study, according to an embodiment of the present invention.

FIG. 2 is a flowchart illustrating an image capture and storage workflow for a medical image study. In step 200, a patient is scanned on a modality that captures medical images using the imaging equipment 122. As used herein the term "medical images" can include any type of diagnostic image. In step 202, the captured medical images are converted into a DICOM format using ISO Standard 12052: 2006 ("ISO 12052"). ISO 12052 defines formats for medical images that can be exchanged with the data and quality necessary for clinical use. In another embodiment, the NEMA standard PS3 can also be used to convert the captured medical images into a DICOM format.

In step 204, the DICOM data is archived to the PACS 118, and all of the image series in the study are identified as a group using a unique identifier, such as a study identifier. In step 206, the system determines if the patient requires electronic access to the study. This determination can be made manually by a radiology technician, clinician, or physician (collectively, a "provider") that is performing, supervising, or reading the study, and the determination can be entered into an interface on the virtual machine 124, or alternatively, on the provider workstation 116 or PACS workstation 120 (collectively, the "provider interface"). In another embodiment, the patient can be asked if they would like electronic access to the study during the patient in-take process. In the event the patient does request access, the request can be appended to the patient's medical file or chart, and this request can be automatically transferred to the PACS 118, relayed to the provider, or annotated as a note with the patient's medical file.

If it is determined that the patient does not require electronic access to the study, the process ends at step 208. If, however, the patient has requested electronic access to the study, the process continues to step 210, where the provider can select the study images to share via the provider interface. Upon selecting the study, an access code is generated by the web application node server 106, and the access code can be transmitted to a web-based interface on the virtual machine 124. This process is described in more detail in FIG. 3 below.

The unique identifier associated with each study is also associated with the access code, as well as patient-specific information, and a PACS lookup location. The patient-specific information, can include, for example, a date of birth, a social security number, an address, a telephone number, or any other unique character string related to the patient. The access code, the patient specific information, the PACS lookup location, and the unique identifier are all stored in the relational database 108, and a backup copy is also stored in a backup relational database 102.

Regarding the PACS lookup location, different image series within the medical image study can be stored at different DICOM locations, and such images may be distributed throughout a cloud-based environment. When the provider enters a query for a particular study, all image series within a single study, even if residing in various DICOM locations, are retrieved, and the provider is presented within a consolidated list of images for the study. In an embodiment, a plurality of databases is communicatively coupled to the data exchange network 100. Images within the medical image study can be stored on different databases (i.e., at different network locations). In yet another embodiment, portions of images can be stored on different databases, such that multiple databases need to be accessed in order to retrieve a full image composed of fragmented portions stored throughout the data exchange network 100.

In step 212, the access code is shared through physical printing (either on-site or to a remote printer), facsimile, secure electronic mail, messaging via the HL7 format, direct message via a Health Information Service Provider (HISP) and/or copied to an electronic clipboard to be pasted into an electronic file, document, medical record, PACS record, electronic mail message, social media message, and/or text message.

In another embodiment, the access code is transmitted via text message, multimedia message, direct social message, a social media post, and/or converted into a URL or URL short-link that can be accessed and viewed on a desktop or mobile-enabled browser.

In another embodiment, the access code can be made available for a limited duration. After expiry of this duration, the access code is no longer valid, and cannot be used to access the study images. Either the patient, or provider, can set a duration for the access code. In another embodiment, the access code be configured for a "one-time" use, such that once a recipient uses the access code, it will not longer be valid and useable for a subsequent access to the medical data.

In yet another embodiment, the access code can be made available via a smartphone application or website, where the application or website only displays the access code for a limited duration. After expiry of this duration, the access code is no longer visible or valid. In one aspect, the application or website can effectively "erase" the access code, similar to how social media posts and messages in the social application Snapchat disappear from view after a certain period of time.

Figure 3:
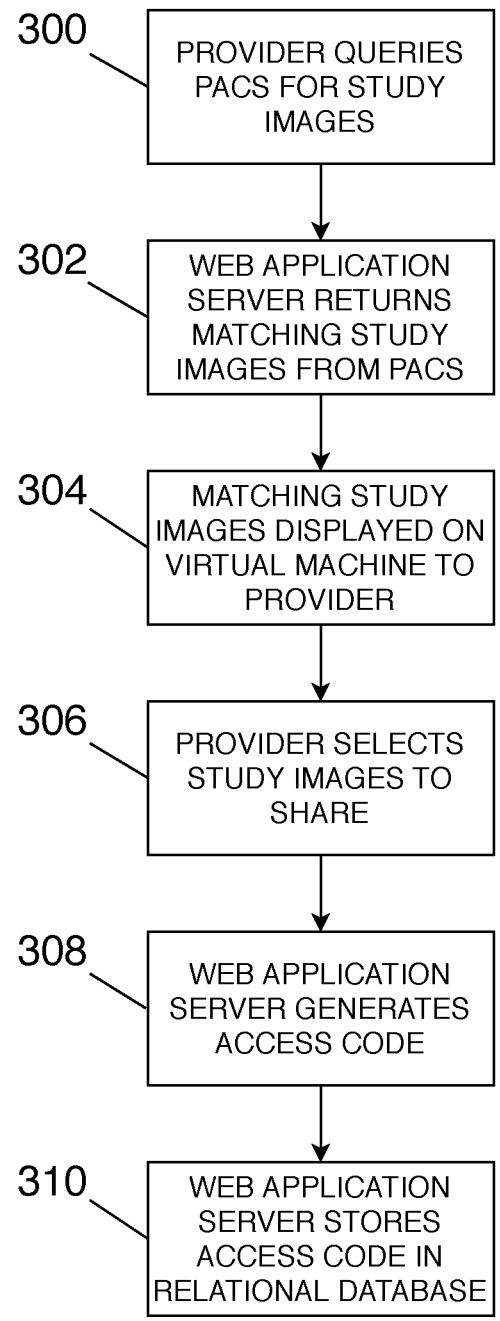
FIG. 3 is a flowchart illustrating an access code generation workflow for a medical image study, according to an embodiment of the present invention.

FIG. 3 is a flowchart illustrating an access code generation workflow for a medical image study. In step 300, the provider queries the PACS 118 via the provider interface. In step 302, the query is transmitted to the web application node server 106, which accesses the relational database 108, and retrieves the matching study images from the PACS 118. The matching can comprise a matching of property or criteria entering on the provider interface, such as, for example, a study identifier, patent-specific information, provider name, provider address, National Provider Identifier (NPI), provider organization, facility name provider specialty, provider and/or facility geographic location, patient age, patient sex, modality, and/or equipment type, or any other criteria. The matching study images are transmitted to the virtual machine 124 (i.e., the provider interface, as discussed above), for viewing and selection by the provider in step 304. In step 306, the provider selects the desired study images, or alternatively, can opt to select all images, via the provider interface. In step 308, an indication of the selected study images is transmitted to the web application node server 106, and the web application node server 106 generates an access code for the selected study images. In step 310, the web application node server 106 stores the access code in the relational database 108, along with the patient specific information, the PACS lookup location, and the unique identifier for the study.

Figure 4:
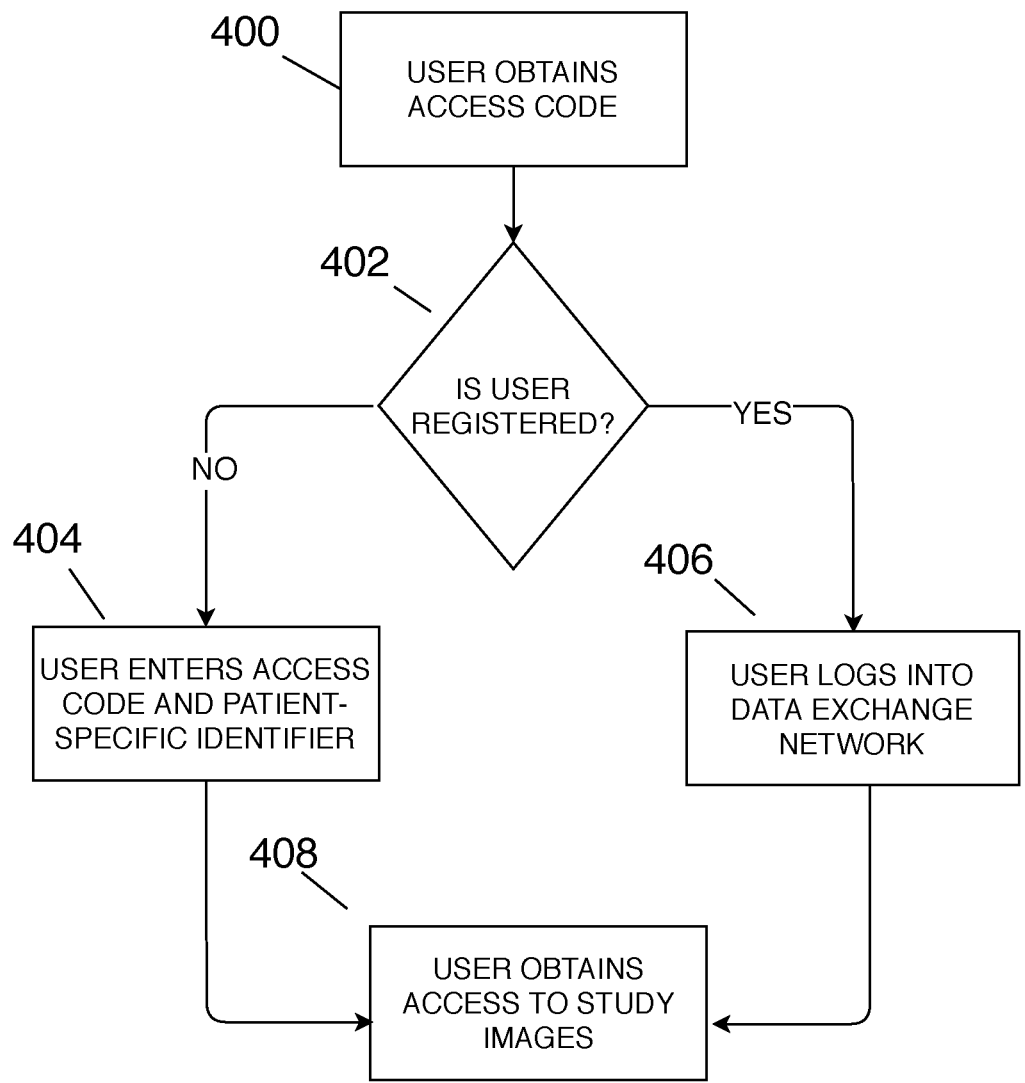
FIG. 4 is a flowchart illustrating a medical image study retrieval workflow using an access code, according to an embodiment of the present invention.

FIG. 4 is a flowchart illustrating a study image retrieval workflow using an access code. In step 400, a user, such as a patient, caretaker, physician, nurse, guardian, etc. obtains the access code. As discussed above, the access code can be physically printed and provided to the user, or the access code can be electronically transmitted to the user. The user can navigate, using a web browser, to a secure website link provided with, or related to, the access code. In the event the user's web browser is not compatible with the website, the data exchange network 100 is configured to initiate the launch of a lightweight browser, such as a lightweight or bundled DICOM image browser or PACS.

In step 402, the system determines if the user is registered with the data exchange network 100. If the user is not registered with the data exchange network 100, the process continues to step 404 where the user enters the access code and the patient-specific identifier, such as a date of birth, a social security number, an address, a telephone number, or any other unique character string related to the patient via a user interface on the user device 128. The user is also provided the option to create an account and become registered with the data exchange network 100.

If, however, the user is already registered with the data exchange network 100, the user can enter their login information, and then enter the access code and patient-specific identifier to access the study images via the user interface on the user device 128 in step 406.

Next, once the user has accessed their study images via step 404 or step 406, the user can view their study images, as well as share, and manage access to third-parties, of their study images in step 408. In an embodiment, if the user is not registered with the data exchange network 100, and if the user chooses not to create an account with the data exchange network 100, access to the study images may be limited for a limited duration, such as 24 hours, 30 days, 1 year etc. This duration can be set by the provider, data exchange network administrator, the patient, HIPPA guidelines, etc.

FIG. 5 is an exemplary user interface for accessing a medical image study using an access code. The access code can be numeric, alphanumeric, or alphabetic, and may also contain special characters. In an embodiment, the access code is randomly generated by the web application node server 106 using cryptographic protocols, hashing algorithms, key-based encryption, obfuscation, and the like. In another embodiment, the access code can be a standard barcode or a matrix barcode, such as a Quick Response ("QR") code, Snapcode, two-dimensional barcode, three-dimensional barcode, SnapTag, SPARQCode, and the like.

Figure 6:
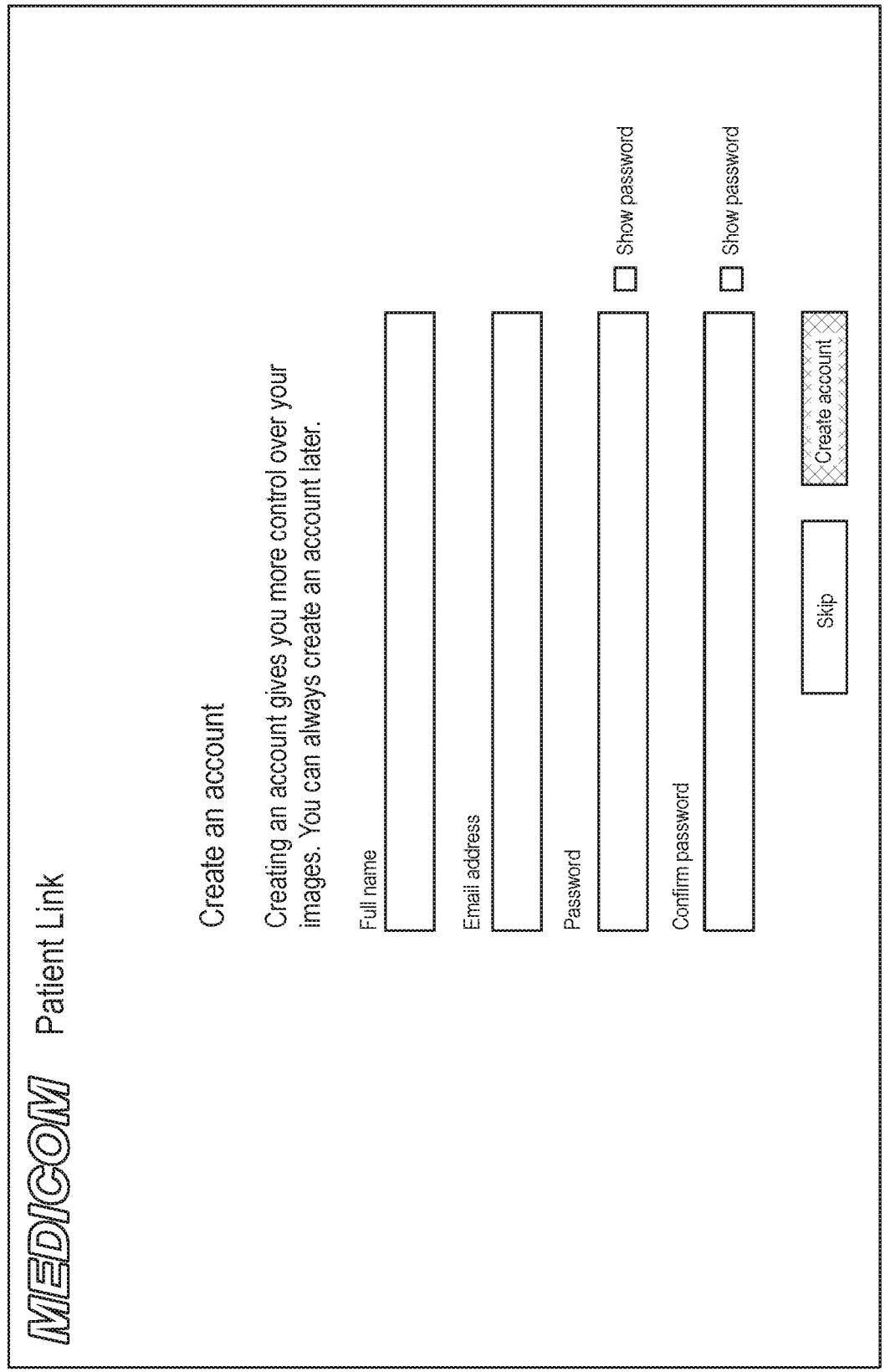
FIG. 6 is an exemplary account registration interface, according to an embodiment of the present invention.

FIG. 6 is an exemplary account registration interface where a user can register with the data exchange network 100. In addition to an alphanumeric password, the user can be provided the option to enable biometric authentication, such as, for example, using fingerprint, iris, facial, gesture, and/or voice recognition. In another embodiment, the user can enable two-factor authentication so that a second device or authentication code is required to authenticate the user.

FIG. 7 is an exemplary medical image study selection interface. Users can select images from multiple studies for a patient, such as a tomography study and CT study, as shown in FIG. 7. In another embodiment, a physician or caretaker that has access to studies for multiple patients can view studies across all of their patients within the interface. In this embodiment, the user can select and filter between patients and patient types (i.e., male, female, age, modality, imaging center, referring physician, date, etc.). The physician can then share study images from multiple patients with third-parties, such as colleagues, primary care physicians, etc.

In an alternative embodiment, however, a single access code is associated with only a single patient, such that study images from multiple patients cannot be viewed on the medical image study selection interface.

The access code can be transmitted along with instructions detailing the recipient address, if sent via electronic mail, facsimile, text message, multimedia message, direct message, or social message.

FIG. 8 is an exemplary electronic mail sharing interface, and FIG. 9 is an exemplary facsimile sharing interface. As discussed above, study images can be shared via text message, multimedia message, direct social message, a social media post, and/or converted into a URL or URL short-link that can be accessed and viewed on a desktop or mobile-enabled browser.

Figure 10:
FIG. 10 is an exemplary copy sharing interface, according to an embodiment of the present invention.

FIG. 10 is an exemplary copy sharing interface. The access code, as well as a web-enabled link and patient-specific identifier, such as the date of birth, is provided in a text format. The user can select and copy this text, and paste it into an electronic file, document, medical record, PACS record, electronic mail message, social media message, and/or text message.

Figure 11:
FIG. 11 is an exemplary printing interface, according to an embodiment of the present invention.

FIG. 11 is an exemplary printing interface, according to an embodiment of the present invention. With the printing option, the user can print the access code and related instructions, or the user can generate a PDF, C-CDA, or image file that can be electronically transmitted to third-party recipient.

Once a recipient receives the access code and views the medical study images, the recipient can download full resolution versions of the images through the peer-to-peer communication channel 126, view the study images using a lightweight or encapsulated DICOM image viewer, or import/download the study images into a native or local PACS. Access to specific features and commands may be restricted based on whether or not the recipient is registered with the data exchange network 100 or not. For example, if the recipient is not registered, the user may not have the ability to download the study images to a local storage location.

Figure 12:
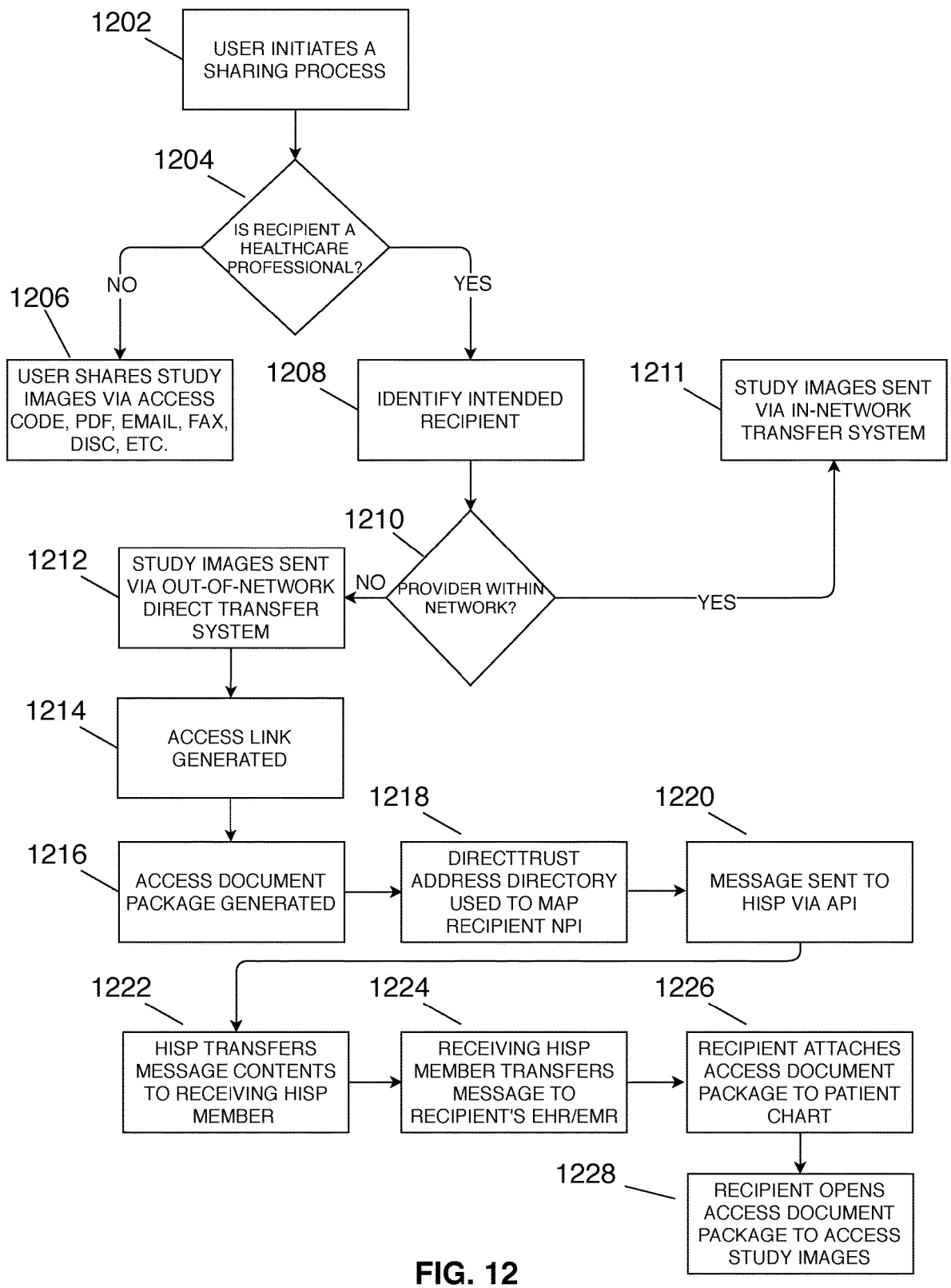
FIG. 12 is a flowchart illustrating a medical image study sharing workflow between a user and a healthcare professional.

FIG. 12 is a flowchart illustrating a medical image study sharing workflow between a user and a healthcare professional. In step 1202, the user initiates a sharing process for a study or study images. In step 1204, the user determines whether the recipient is a healthcare professional. If the recipient is not a healthcare professional, the workflows described above for FIGS. 3 and 4 are commenced in step 1206. In an embodiment, a CPU of the web application node server 106 is configured to initiate the workflows described above for FIGS. 3 and 4 related to generating an access code.

If, however, the recipient is deemed to be a healthcare professional, then in step 1208, the user is prompted to identify the intended recipient or organization. The identification can be entered manually, or the user can be provided with a list of registered recipients, locations, facilities, etc. that can be searched and filtered. In an embodiment, the user interface can include an auto-completion search box, such that as the user types the name of a recipient, a list of matching names is displayed for selection. In another embodiment, the user can search for recipients with, for example, name, address, NPI, organization, specialty, and geographic location. In an embodiment, the CPU of the web application node server 106 is configured to initiate the workflows described in steps 1210 onward.

In step 1210, the system determines if the recipient is registered with the data exchange network 100. If not, then the study images are shared in step 1211 using an in-network secure peer-to-peer communication system that is described in commonly owed U.S. patent application Ser. No. 15/361,319, filed on Nov. 25, 2016, and entitled, "METHODS AND SYSTEMS FOR PROVIDING SECURE AND AUDITABLE TRANSFER OF ENCRYPTED DATA BETWEEN REMOTE LOCATIONS", which is hereby incorporated by reference in its entirety.

If the recipient is deemed to be registered with the data exchange network 100, then in step 124, then the study images are shared in step 1212 using an out-of-network direct transmission method described in commonly owed U.S. patent application Ser. No. 15/361,320, filed on Nov. 25, 2016, and entitled, "METHODS AND SYSTEMS FOR TRANSFERRING SECURE DATA AND FACILITATING NEW CLIENT ACQUISITIONS", which is hereby incorporated by reference in its entirety.

In the direct transmission method, the system generates an access link in step 1214, and subsequently generates an access document package in step 1216, where the access document package can include study images, electronic medical records, and any other patient-related data or information. The access document package, in an embodiment, can be a PDF and/or C-CDA document that is populated with document guidelines, an access link to the full study, embedded key image sets, and radiology reports and/or notations. In yet another embodiment, the access document package can be an encapsulated image file, such as a JPEG, GIF, PNG, or BMP file.

The access document package is transmitted to a Direct-Trust address directory in step 1218, where the DirectTrust address is associated/mapped with the recipient's unique NPI. In step 1220, the access document package is transmitted to a HISP via an application program interface (API), such as the HISPDirect API or Rest Implementation. In step 1222, the HISP transfers the access document package via the DirectTrust protocol to a receiving HISP member. In step 1224, the receiving HISP member transfers the access document package to a recipient's DirectTrust-enabled electronic health record or electronic medical record file or database. Once received, the recipient can attach, link, embed, or otherwise associate the access document package to the patient's chart, file, medical record, or database in step 1226. The recipient can then open the access document package and access the contents in step 1228.

The foregoing description of a preferred embodiment and best mode of the invention known to the applicant at this time of filing the application has been presented and is intended for the purposes of illustration and description. It is not intended to be exhaustive or limit the invention to the precise form disclosed and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out the invention.

As such, the present invention is not limited to use within a medical environment, and the invention may be used to directly and securely transfer financial, military, video, multimedia, audio, personally identifiable, and other sensitive information between to remote locations without storing the data on an intermediary server, thereby allowing a direct transfer of encrypted data irrespective of the content-type, and without utilizing the intermediary server for storage of the transmitted data, and by providing an access code to the recipient for authorization purposes.

What is claimed is:

1. A method of providing secure access to a medical image study, comprising:

generating, by a server, an encrypted access code containing a study identifier and at least one network location;

receiving, from a user device, an instruction to transmit the access code to at least one recipient device, wherein the transmission medium is selected from a group consisting of electronic mail, facsimile, SMS messaging, direct messaging, and secure messaging, the instruction further including a recipient address; and transmitting, by the server, the access code to the recipient device based on the transmission medium specified in the instruction, wherein the study identifier is associated with a plurality of diagnostic images stored on a plurality of databases coupled to the server, and wherein the network location corresponds to network addresses of databases with diagnostic images containing the study identifier, and wherein the recipient device is allowed access to the diagnostic images via an encapsulated viewer upon the recipient device transmitting the access code to the server.

2. The method of claim 1, wherein direct messaging includes the Health Information Service Provider (HISP) Direct framework.

3. The method of claim 2, wherein the access code is valid for a predetermined duration.

4. The method of claim 2, wherein the recipient device is granted permission to download the diagnostic images if the recipient device is registered with the server.

5. The method of claim 2, wherein the recipient device is restricted from downloading the diagnostic images if the recipient device is not registered with the server.

6. The method of claim 2, wherein the recipient device is required to provide the access code and a patient-specific identifier to the server in order to access the diagnostic images.

7. The method of claim 6, wherein the patient-specific identifier is selected from a group consisting of a date of birth, a social security number, an address, and a telephone number.

* * * * *